(12) United States Patent
Exelmans et al.

(10) Patent No.: US 10,755,450 B2
(45) Date of Patent: Aug. 25, 2020

(54) DISPLAY OF DEPTH LOCATION OF COMPUTED TOMOGRAPHY SLICE IMAGES RELATIVE TO AN OBJECT TO BE IMAGED

(71) Applicant: AGFA NV, Mortsel (BE)

(72) Inventors: Walter Exelmans, Mortsel (BE); Jeroen Cant, Mortsel (BE)

(73) Assignee: AGFA NV, Morstel (BE)

( * ) Notice: Subject to any disclaimer, the term of this patent is extended or adjusted under 35 U.S.C. 154(b) by 0 days.

(21) Appl. No.: 15/741,308

(22) PCT Filed: Jun. 29, 2016

(86) PCT No.: PCT/EP2016/065094
§ 371 (c)(1),
(2) Date: Jan. 2, 2018

(87) PCT Pub. No.: WO2017/005566
PCT Pub. Date: Jan. 12, 2017

(65) Prior Publication Data
US 2018/0197316 A1    Jul. 12, 2018

(30) Foreign Application Priority Data
Jul. 3, 2015  (EP) .................................. 15175174

(51) Int. Cl.
*G06T 11/00* (2006.01)
*A61B 6/02* (2006.01)
*A61B 6/08* (2006.01)
*A61B 90/00* (2016.01)

(52) U.S. Cl.
CPC ............ *G06T 11/005* (2013.01); *A61B 6/025* (2013.01); *A61B 6/08* (2013.01); *A61B 2090/366* (2016.02)

(58) Field of Classification Search
CPC combination set(s) only.
See application file for complete search history.

(56) References Cited

U.S. PATENT DOCUMENTS

| | | | | |
|---|---|---|---|---|
| 4,442,533 A | * | 4/1984 | Lescrenier | A61B 6/0457 378/206 |
| 4,702,257 A | * | 10/1987 | Moriyama | A61B 5/0555 378/4 |
| 5,188,110 A | * | 2/1993 | Sugimoto | A61B 6/032 378/20 |
| 5,577,095 A | * | 11/1996 | Kobayashi | A61B 6/032 378/205 |
| 6,061,420 A | | 5/2000 | Strong et al. | |
| 7,630,533 B2 | * | 12/2009 | Ruth | A61B 6/502 382/131 |

(Continued)

FOREIGN PATENT DOCUMENTS

DE  10 2012 216 850 B3   2/2014

OTHER PUBLICATIONS

Official Communication issued in International Patent Application No. PCT/EP2016/065094, dated Aug. 25, 2016.

*Primary Examiner* — Tsung Yin Tsai
(74) *Attorney, Agent, or Firm* — Stinson LLP

(57) ABSTRACT

A visual indication is generated of depth locations of slices obtained by applying a reconstruction algorithm in a computed tomography method with given settings, the display being shown on the object, e.g. on the patient's lateral side or in close relation to the patient.

11 Claims, 4 Drawing Sheets

(56) References Cited

U.S. PATENT DOCUMENTS

| | | | | |
|---|---|---|---|---|
| 8,147,503 B2* | 4/2012 | Zhao | ............... | G06K 9/3241 |
| | | | | 382/128 |
| 8,371,751 B2* | 2/2013 | Vazquez | ............ | A61B 5/1128 |
| | | | | 378/206 |
| 2002/0077533 A1* | 6/2002 | Bieger | ............... | A61B 34/20 |
| | | | | 600/300 |
| 2009/0285357 A1* | 11/2009 | Khamene | ............ | A61B 6/5217 |
| | | | | 378/20 |
| 2010/0141654 A1* | 6/2010 | Neemuchwala | ..... | A61B 8/5223 |
| | | | | 345/427 |
| 2011/0102430 A1* | 5/2011 | Eberhard | ............ | G06T 11/008 |
| | | | | 345/420 |
| 2011/0110576 A1* | 5/2011 | Kreeger | ............... | G16H 50/20 |
| | | | | 382/132 |
| 2011/0142196 A1* | 6/2011 | Shinno | ............... | A61B 6/08 |
| | | | | 378/20 |
| 2012/0123252 A1* | 5/2012 | Brunner | ............ | A61B 8/4254 |
| | | | | 600/425 |
| 2014/0033126 A1* | 1/2014 | Kreeger | ............ | G06F 3/04817 |
| | | | | 715/821 |
| 2014/0121636 A1* | 5/2014 | Boyden | ............... | A61B 90/11 |
| | | | | 604/506 |
| 2015/0011285 A1* | 1/2015 | Kaiblinger | ............ | G07C 15/00 |
| | | | | 463/16 |
| 2015/0208989 A1 | 7/2015 | Rackow et al. | | |
| 2015/0293600 A1* | 10/2015 | Sears | ............... | H04N 13/271 |
| | | | | 345/156 |
| 2015/0302594 A1* | 10/2015 | Moore | ............... | G01B 11/25 |
| | | | | 348/47 |
| 2016/0324580 A1* | 11/2016 | Esterberg | ............ | A61B 5/055 |
| 2017/0261442 A1* | 9/2017 | Yun | ............... | H01J 35/08 |
| 2019/0311542 A1* | 10/2019 | Douglas | ............ | A61B 6/466 |

* cited by examiner

DISPLAY OF DEPTH LOCATION OF COMPUTED TOMOGRAPHY SLICE IMAGES RELATIVE TO AN OBJECT TO BE IMAGED

CROSS REFERENCE TO RELATED APPLICATIONS

This application is a 371 National Stage Application of PCT/EP2016/065094, filed Jun. 29, 2016. This application claims the benefit of European Application No. 15175174.0, filed Jul. 3, 2015, which is incorporated by reference herein in its entirety.

BACKGROUND OF THE INVENTION

1. Field of the Invention

The present invention relates to a computed tomography imaging method such as a tomosynthesis imaging method.

2. Description of the Related Art

Digital tomosynthesis is a radiographic imaging technique that comprises a first step of acquiring X-ray projection images (also called x-ray projections) by irradiating a patient or object with a cone shaped x-ray beam emitted from different directions and detecting the x-ray projection images by means of a radiation detector such as a direct radiography detector, and generating a digital representation of these projection images. Typically the x-ray source is moved over a limited angle around the patient or object, e.g. 15 to 60 degrees, and a limited number of discrete exposures are performed typically 30 to 45 exposures.

The method comprises a second step in which from these projection images slice images at different depths within the patient or object that is examined, are computed. The slice images are computed by applying a reconstruction algorithm to the acquired projection images.

Reconstruction algorithms for tomosynthesis solve the inverse problem that can be written as $$Ax = p \quad (1)$$

where A represents the projection operator, x is the vectorized representation of the x-ray attenuation coefficients of the object or patient and p the measured data or projection images.

In the presence of noise, (1) cannot be solved exactly and reconstruction algorithms are therefore designed to solve the following problem:

$$\|Ax - p\| < \varepsilon \quad (2)$$

Where $\varepsilon$ is a constant that depends on the noise in the system.

For tomosynthesis, the projection images p are typically acquired with a flat panel detector which has a higher resolution than most CT scanners, resulting in a high in-plane resolution of the reconstruction. However, due to the limited angle from which exposures are taken the problem is typically ill defined in the direction perpendicular to the detector. This results in a limited depth resolution.

Different reconstruction algorithms exist that either solve (1) or (2) analytically (e.g. FDK, filtered backprojection, . . . ) or iteratively (e.g. Maximum Likelihood Expectation Maximization, algebraic reconstruction methods such as SIRT, SART, etc).

The inverse problem (2) can also be extended with regularization and be written as $$\min_x \ \|Ax - p\| + \lambda \|Lx\|$$

where $\lambda$ is a weight factor and L a cost function that incorporates prior knowledge into the problem. An example of such prior knowledge for medical images is the assumption that the image is piecewise constant and hence L minimizes the Total Variation of x.

Once the digital data representing the projection images are acquired, a series of slices at different depths and different thicknesses may be reconstructed from the same acquisition.

Since tomosynthesis is a computed imaging technique there is no direct interpretable correspondence between the acquired projection images and the sliced images resulting from computation applied to the set of projection images. It is thus difficult for the physician or the radiologist to judge in advance what the result of the computation will be. More specifically, it is hard to judge in advance whether the acquisition of the projection images with the set x-ray source settings and the input settings of the reconstruction algorithm will lead to slice images that give the information to the radiologist or the physician he is envisaging to obtain.

More specifically it is hard to judge in advance whether the depth location of the slice images relative to the patient is adequate for the radiologist or physician to perform a specific examination of certain organs or body parts.

The problem has been described with reference to tomosynthesis but is likewise applicable to other computer tomography techniques among which are cone beam computed tomography, laminography etc.

SUMMARY OF THE INVENTION

Preferred embodiments of this invention overcome the above-described problems.

The above-mentioned aspects are realised by a method having the specific method steps set out below.

Specific elements of preferred embodiments of the invention are also set out below.

The invention is advantageous in that it provides feedback to the physician or to the radiologist on the depth location of the slices relative to the patient.

Because tomographic imaging is a computed imaging method based on the processing of projection images, there is no direct feedback on the location of the slice images that will ultimately be obtained by the imaging and reconstruction method.

It might thus very well be that the locations of the slice images computed with certain settings do not provide the optimal results for assisting the examination.

The invention provides assistance to the user (radiologist, physician, . . . ) in his search for optimal location of the slices so as to obtain a set of slice images the location of which optimally corresponds with the location of the inner parts of the body the radiologist or physician envisages to examine.

In case the location of the slice images is not satisfactory, parameters of the reconstruction algorithm can be adapted so that the locations of the resulting slice images better correspond with the desired locations (better corresponds with the location of organs or inner parts of the body he wants to examine).

Further advantages and embodiments of the present invention will become apparent from the following description and drawings.

DETAILED DESCRIPTION OF THE PREFERRED EMBODIMENTS

Figure 1:
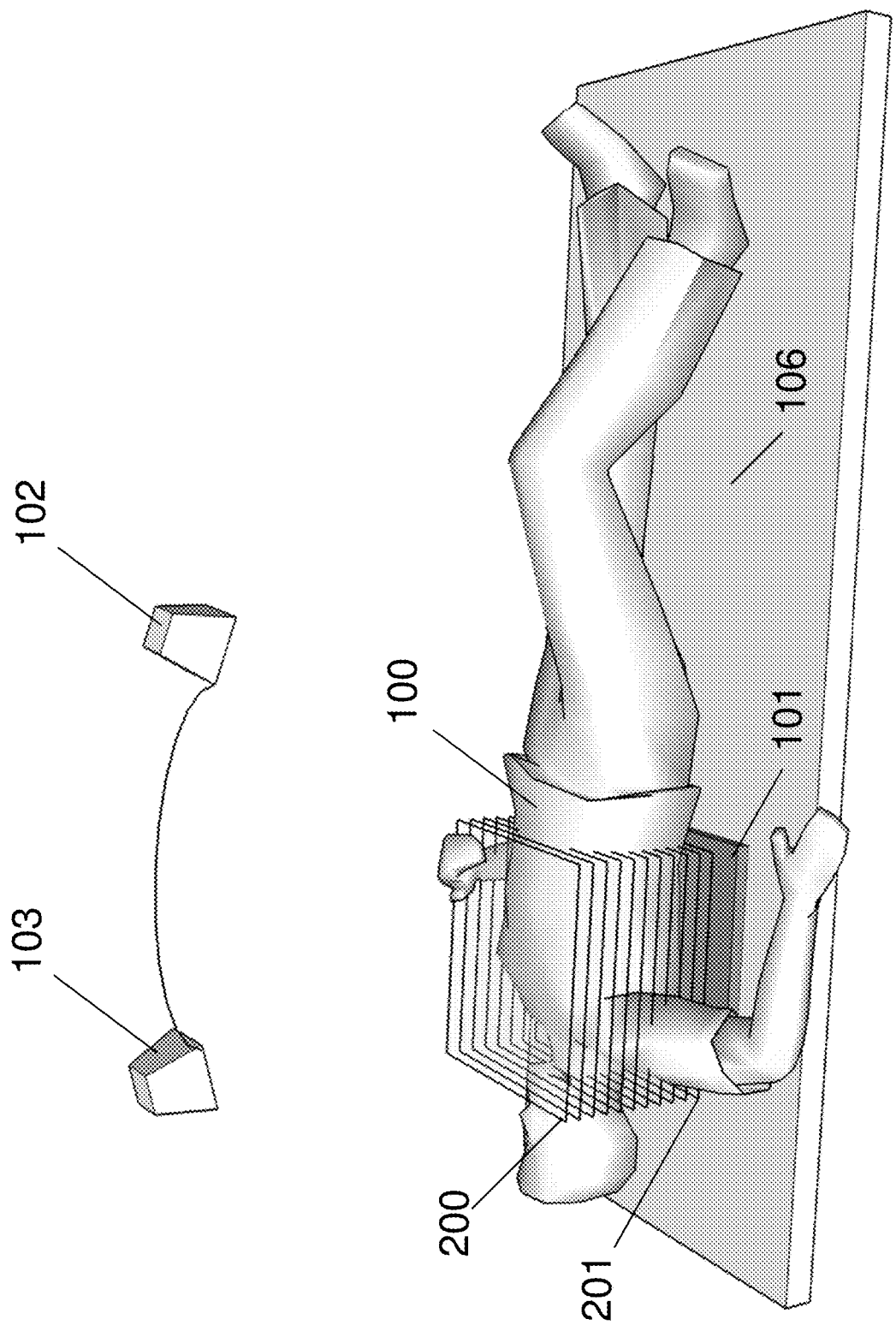
FIG. 1 illustrates a tomosynthesis imaging process in general.

FIG. 1 generally illustrates a tomosynthesis imaging procedure.

The figure shows a source of x-rays which can be moved along a pre-defined path from a first position 102 to a second position 103.

The angular range of the source movement in tomosynthesis is limited, the rotation angle is typically between 15° and 60° around the patient, in many cases it is between 30° and 45° (whereas in conventional computed tomography the rotational angle around the patient is 360°). X-rays emitted by the source in a limited number of positions are directed towards a patient 100 who is positioned in an x-ray examination room on a supporting table 106.

A radiation detector such as a direct radiography detector is provided behind the patient so that x-rays which reach the patient and the intensity of which is modulated by the patient's body are detected and converted into an electrical signal representation.

In a tomosynthesis imaging method, radiation emitted in a discrete number of positions between first position 102 and second position 103 are detected by the radiation detector 101 and are converted into digital so-called projection images.

A reconstruction algorithm is applied to the projection images which are generated with the x-ray source positioned at different angles.

Several reconstruction algorithms for tomosynthesis imaging are known. Among these are an iterative algebraic reconstruction technique, reconstruction based on maximum likelihood etc.

By this reconstruction algorithm a number of so-called slice images are computed which represent a x-ray image of the examined body at different depths (depth being defined in z-direction perpendicular to an x,y plane in which the examined body is mainly positioned).

FIG. 1 schematically shows such slice images. Slice images are images in parallel planes, substantially parallel to the detector plane. In FIG. 1 a number of slices are shown, slice 200 being the first reconstructed slice (lowest depth, seen from the x-ray source position) and slice 201 being the last reconstructed slice (largest depth seen from the x-ray source position).

Starting from a set of projection images obtained by irradiating the patient by x-rays emitted by a source of radiation under different angles relative to the patient (with the x-ray source in different positions) and detecting these projection images by direct radiography detector 101, a reconstruction algorithm can be applied to compute a set number of slices at envisaged depths within the body of the patient who is examined.

For this purpose the system comprises a controller/processor 107 which receives as input the data representing the projection images obtained by the different discrete irradiation steps.

The reconstruction algorithm additionally is fed with data on the exposure angles at which the x-ray source is positioned when irradiating the patient, the projection distance being the distance between the radiation source and the radiation detector 101.

Depending on the location inside the patient the radiologist is interested in, slice images at particular depths will be more interesting than slice images at other depths.

As will be described further on, the present invention is advantageous in that it provides to the radiologist an indication of the location of the slice images relative to the patient.

Figure 2:
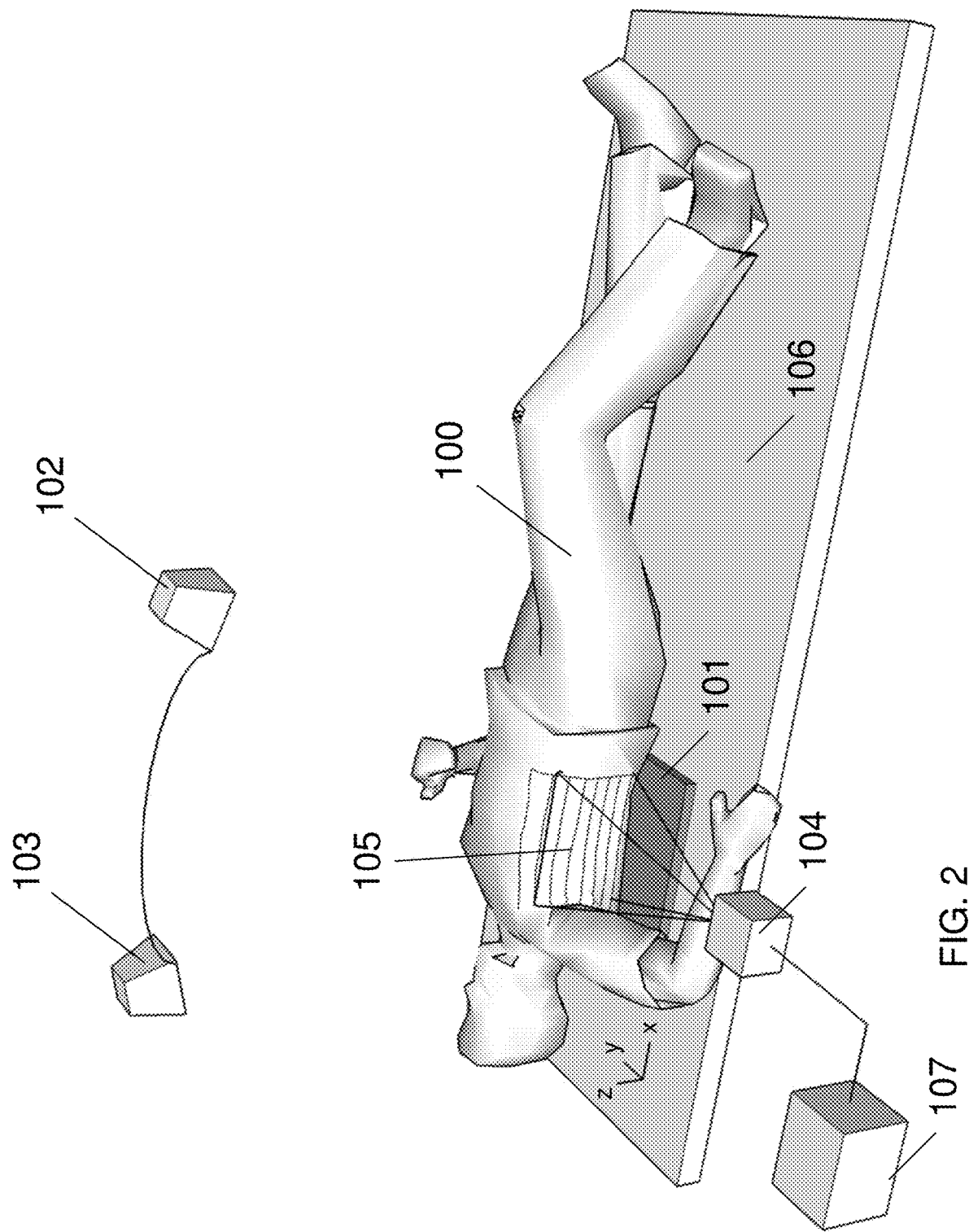
FIG. 2 illustrates the display of the location of a tomosynthesis image slices on a patient.

FIG. 2 shows a similar set up as that of FIG. 1. Additionally the output of controller/processor 107 is coupled to means for projecting a visual indication of the location of the slices, e.g. a laser projector 104 (or a beamer or another type of light projecting device).

According to an embodiment of this invention, the controller/processor 107 is arranged to compute the location of the slices in the z-direction (depth of the location of the slice images) which correspond with certain settings such as exposure angles, projection distance, envisaged number of slices and the slice thickness.

Slice thickness is a parameter for which a value can be input to the processor 107. Alternatively the location of the upper and the lower slice as well as the envisaged number of slices can be input and the sliced thickness can be deduced from these values.

The calculated depth location data are fed to a projector 104, for example a laser projector, that projects a number of horizontal lines indicative of the depth of each of the set of slice images onto the lateral side of the patient. By the notion 'lateral side' is meant the side that is perpendicular to the side that is irradiated by the x-rays source in the different angular positions in between location 102 and location 103.

Projector 104 can be a laser projector. However other means can be envisaged for projecting a visual indication of the depth location of the slices onto the patient. Examples of other suitable means are a beamer, . . . .

In the illustrated embodiment in FIG. 2, the location of the different slices is illustrated as a horizontal full line. Alternatives may be envisaged such as one or more dots, . . . .

In still another embodiment slices could be numbered or named and such number or name could be projected onto the patient's body.

In one embodiment the depth location of all calculated slices is shown. Alternatively it is also possible that only the location of some of the computed slices is shown, for example the upper and lowest slice (upper being the top slice in the z-direction, lowest being the slice that is situated at the largest depth within the patient's body).

In still another element the location of each of the different calculated slices is shown as a sequence of indications (e.g. horizontal lines) projected consecutively.

In another embodiment the position of the computed slices is not projected onto the patient's body itself but onto a means which stands in a fixed relation to the depth direction in the patient.

Figure 3:
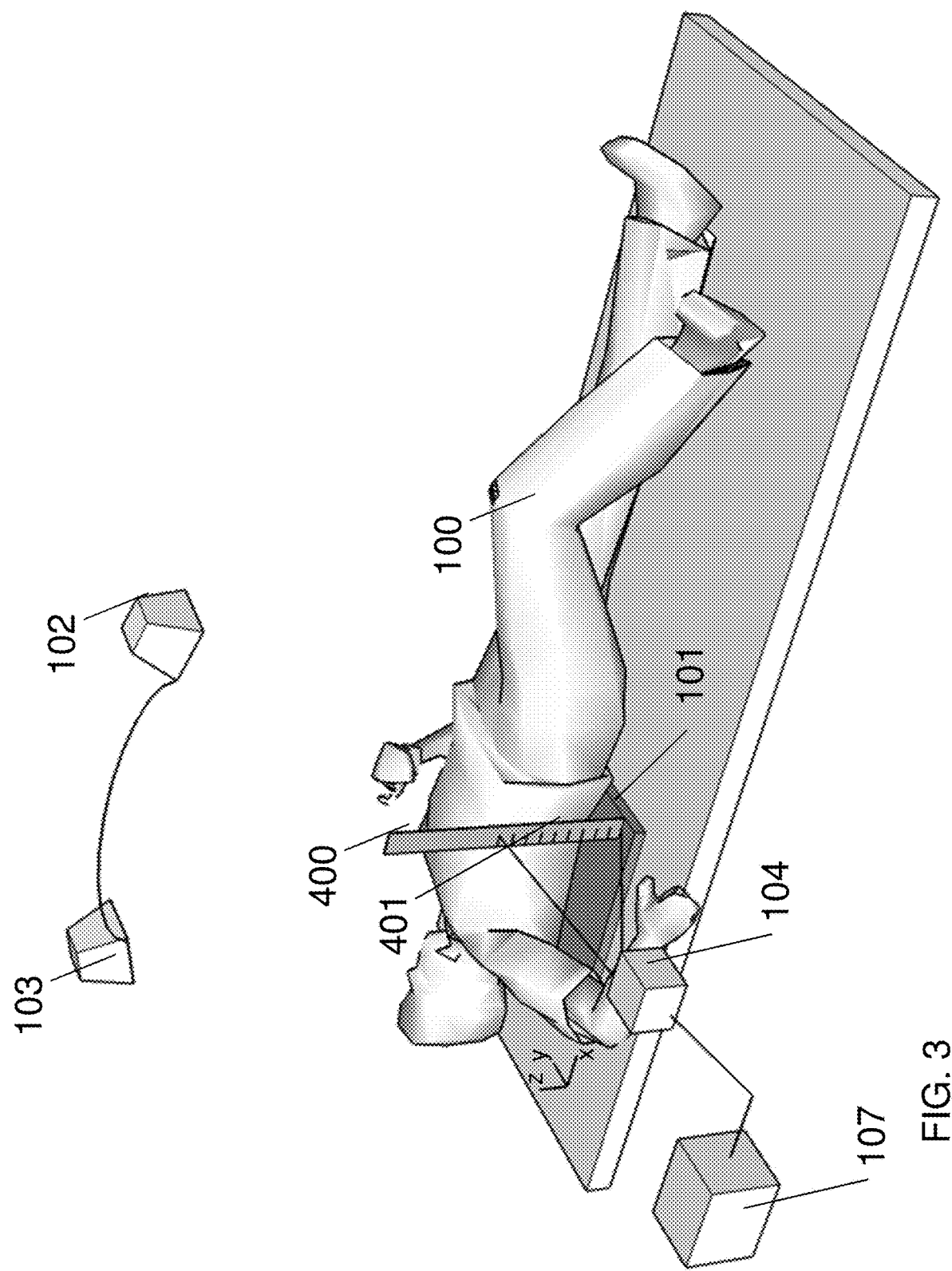
FIG. 3 shows the location of tomosynthesis slices on a ruler located next to a patient in a known positional relationship to the patient.
Figure 4:
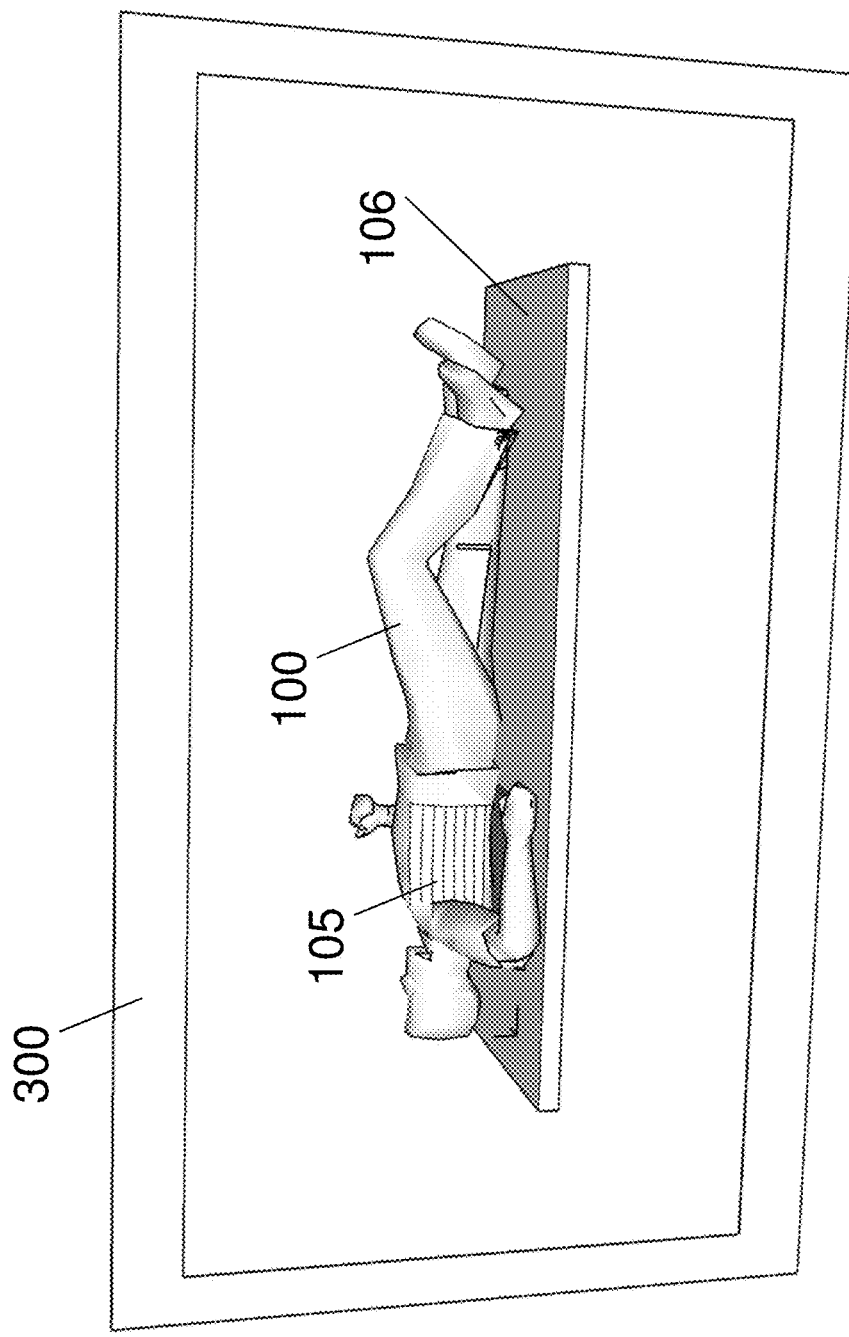
FIG. 4 shows the display screen of a display device on which the location of tomosynthesis slices relative to the patient is shown.

FIG. 3 shows such an alternative. This figure shows a similar setup as that of FIGS. 1 and 2, however in this figure a ruler 401 is shown which is located adjacent to the patient parallel to the z-direction.

Projecting means 104 are arranged to emit light so that the locations of the different slices are projected onto ruler 401.

In addition to the display of the location of the slices on the patient or on a means adjacent and in fixed relation to the patient, the location of the slices relative to the patient's body can also be displayed on the screen of a display device that is connected to the controller/processor 107.

Alternatively the location of the slices can additionally be displayed on a display device overlaid on a display of the object, or on a displayed model of the object or on a 3D display of the object acquire e.g. by a set of depth cameras.

Still alternative embodiments may be envisaged.

In addition to the display of the location of each of or at least some of the slices that would be obtained by applying the reconstruction algorithm with the settings that are input to the algorithm, one could also display the dose distribution which the patient received during the current tomosynthesis examination.

This dose distribution can be indicated for example by means of varying colours which correspond to different dose levels. This dose distribution can be displayed on the additional display device that is coupled to the controller/processor and receives input from the controller/processor.

According to a specific embodiment of the present invention the location of the slices is evaluated by the user (operator, physician, doctor) in order to see whether the location of the computed slices corresponds with the location in the patient's body which the doctor wants to examine.

In case the locations are not adequate for the envisaged examination of the patient or do simply not correspond with the expectations of the doctor, the parameters of the reconstruction algorithm can be adapted and the display of the location of the slices which would be obtained with the adapted settings can again be displayed and evaluated.

Alternatively the patient's position can be changed so that the slice positions are on the envisaged locations.

Still alternatively user-controlled displacement (shifting) of the displayed indications of the slice positions (e.g. the horizontal lines that are displayed on the lateral side of the patient) obtained with a first set of parameters for the reconstruction algorithm, can be performed and parameters for the reconstruction algorithm corresponding with the adapted locations can be determined and applied.

These displacements can be achieved in different ways, such as displacing displayed lines on a user interface on a work station coupled to the system. Alternatives may be envisaged.

Once the depth location of the slices is satisfactory to the doctor the effective imaging can be performed with the settings leading to these locations of the slices.

It will be clear that although the invention has been explained with reference to a tomosynthesis examination of a human patient, this invention is likewise applicable to veterinary applications or to tomosynthesis examination of an object of whatever type.

Having described in detail preferred embodiments of the current invention, it will now be apparent to those skilled in the art that numerous modifications can be made therein without departing from the scope of the invention as defined in the appending claims.

The invention claimed is:

1. A computed tomography imaging method for generating a radiation image of an object, the method comprising the steps of:
    applying a reconstruction algorithm with a set of input parameters to reconstruct tomography slice images at specific locations; and
    generating a visual indication of a depth location of at least one of the tomography slice images that has already been obtained by applying the reconstruction algorithm with the set of input parameters; wherein
    the visual indication is shown in a positional relationship to the object; and
    the visual indication of the depth location of the at least one of the tomography slice images is projected onto the object to indicate the depth location relative to the object.

2. The method according to claim 1, further comprising the steps of:
    evaluating whether the depth location of the least one of the tomography slice images corresponds to an envisaged depth location of the at least one of the tomography slice images; and
    modifying the input parameters so that the depth location of the at least one of the tomography slice images obtained by applying the reconstruction algorithm with the modified input parameters corresponds to the envisaged depth location.

3. The method according to claim 1, wherein the visual indication is projected using a beamer.

4. The method according to claim 1, wherein the visual indication is projected using a laser projector.

5. The method according to claim 1, wherein the step of generating the visual indication of the depth location of the at least one of the tomography slice images includes showing the visual indication in a preset fixed location relative to the object.

6. The method according to claim 5, wherein the step of showing the visual indication includes showing the visual indication on a ruler.

7. The method according to claim 1, further comprising the step of:
    displaying the specific locations overlaid on a displayed image of the object.

8. The method according to claim 1, further comprising the step of:
    displaying the specific locations on a model representing the object.

9. The method according to claim 1, further comprising the step of:
    displaying the specific locations on a 3D image of the object.

10. The method according to a claim 1, further comprising the step of:
    generating a tomographic image of the object with the input parameters of the reconstruction algorithm when the visual indication of the depth location of the at least one of the tomography slice images corresponds to an envisaged depth location of the at least one of the tomography slice images.

11. The method according to claim 1, wherein the computed tomography method is a tomosynthesis imaging method.

* * * * *